US007015175B2

(12) United States Patent
Vassilakis et al.

(10) Patent No.: US 7,015,175 B2
(45) Date of Patent: Mar. 21, 2006

(54) HIGH-ACTIVITY ISOMERIZATION CATALYST AND PROCESS

(75) Inventors: James G. Vassilakis, Naperville, IL (US); Richard R. Rosin, Glencoe, IL (US); Steven A. Bradley, Arlington Heights, IL (US); Ralph D. Gillespie, Gurnee, IL (US); Michelle J. Cohn, Glenview, IL (US); Feng Xu, Buffalo Grove, IL (US)

(73) Assignee: UOP LLC, Des Moines, IL (US)

( * ) Notice: Subject to any disclaimer, the term of this patent is extended or adjusted under 35 U.S.C. 154(b) by 25 days.

(21) Appl. No.: 10/872,581

(22) Filed: Jun. 21, 2004

(65) Prior Publication Data

US 2005/0027154 A1 Feb. 3, 2005

Related U.S. Application Data (60) Continuation-in-part of application No. 10/804,358, filed on Mar. 19, 2004, which is a continuation-in-part of application No. 10/717,812, filed on Nov. 20, 2003, now Pat. No. 6,881,873, and a continuation-in-part of application No. 10/718,050, filed on Nov. 20, 2003, now Pat. No. 6,927,188, which is a division of application No. 09/942,237, filed on Aug. 29, 2001, now Pat. No. 6,706,659, which is a continuation of application No. 09/942,237, filed on Aug. 29, 2001, now Pat. No. 6,706,659.

(51) Int. Cl.
*B01J 27/053* (2006.01)
*B01J 23/00* (2006.01)
*B01J 23/56* (2006.01)
*C07C 5/22* (2006.01)
*C07C 5/13* (2006.01)

(52) U.S. Cl. ............... 502/217; 502/302; 502/303; 502/332; 502/333; 502/334; 502/339; 585/477; 585/480; 585/482; 585/734; 585/750; 585/751

(58) Field of Classification Search ............... 502/217, 502/302, 303, 332, 333–334, 339; 585/477, 585/480, 482, 734, 750, 751
See application file for complete search history.

(56) References Cited

U.S. PATENT DOCUMENTS 2,939,896 A 6/1960 Myers .................. 260/683.68

(Continued)

FOREIGN PATENT DOCUMENTS

| EP | 0 666 109 A1 | 8/1995 |
| EP | 0983967 A1 | 3/2000 |
| EP | 1002579 A1 | 5/2000 |
| JP | 61242641 A | 10/1986 |

OTHER PUBLICATIONS

Robert A. Meyers, The Handbook of Petroleum Refining Processes, 1986, 5-19 through 5-51, no month.

(Continued)

*Primary Examiner*—J. A. Lorengo
*Assistant Examiner*—Patricia L. Hailey
(74) *Attorney, Agent, or Firm*—John G. Tolomei; Maryann Maas (57) ABSTRACT

A catalyst and process is disclosed to selectively upgrade a paraffinic feedstock to obtain an isoparaffin-rich product for blending into gasoline. The catalyst comprises a support of a sulfated oxide or hydroxide of a Group IVB (IUPAC 4) metal, a first component of at least one lanthanide element or yttrium component, which is preferably ytterbium, and at least one platinum-group metal component which is preferably platinum and a refractory-oxide binder having at least one platinum-group metal component dispersed thereon.

27 Claims, 2 Drawing Sheets

U.S. PATENT DOCUMENTS

| | | | |
|---|---|---|---|
| 2,966,528 A | 12/1960 | Haensel | 260/666 |
| 2,985,589 A | 5/1961 | Broughton et al. | 210/34 |
| 3,040,777 A | 6/1962 | Carson et al. | 137/625.15 |
| 3,175,444 A | 3/1965 | Spinney | 83/251 |
| 3,236,761 A * | 2/1966 | Rabo et al. | 502/74 |
| 3,236,762 A * | 2/1966 | Rabo et al. | 208/111.25 |
| 3,422,848 A | 1/1969 | Liebman et al. | 137/625.15 |
| 3,755,144 A | 8/1973 | Asselin | 208/95 |
| 3,915,845 A | 10/1975 | Antos | 208/139 |
| 4,003,826 A | 1/1977 | Antos | 208/139 |
| 4,024,052 A | 5/1977 | Antos | 208/139 |
| 4,024,077 A | 5/1977 | Engelhard et al. | 252/442 |
| 4,061,724 A | 12/1977 | Grose et al. | 423/335 |
| 4,073,865 A | 2/1978 | Flanigen et al. | 423/339 |
| 4,087,381 A | 5/1978 | Antos | 252/441 |
| 4,241,036 A * | 12/1980 | Flanigen et al. | 502/62 |
| 4,310,440 A | 1/1982 | Wilson et al. | 252/435 |
| 4,331,822 A | 5/1982 | Onodera et al. | 585/482 |
| 4,440,871 A | 4/1984 | Lok et al. | 502/214 |
| 4,485,185 A | 11/1984 | Onodera et al. | 502/71 |
| 4,567,027 A | 1/1986 | Detournay et al. | 423/101 |
| 4,567,029 A | 1/1986 | Wilson et al. | 423/306 |
| 4,709,116 A | 11/1987 | Zarchy et al. | 585/738 |
| 4,709,117 A | 11/1987 | Gray, Jr. | 585/738 |
| 4,717,784 A | 1/1988 | Stem et al. | 585/738 |
| 4,758,419 A | 7/1988 | Lok et al. | 423/306 |
| 4,804,802 A | 2/1989 | Evans et al. | 585/734 |
| 4,804,803 A | 2/1989 | Schmidt et al. | 585/748 |
| 4,834,958 A | 5/1989 | Zones | 423/277 |
| 4,899,012 A | 2/1990 | Sachtler et al. | 585/482 |
| 4,909,116 A | 3/1990 | Tanaka et al. | 84/692 |
| 4,918,041 A | 4/1990 | Hollstein et al. | 502/217 |
| 4,939,110 A | 7/1990 | Sachtler et al. | 502/66 |
| 4,956,519 A | 9/1990 | Hollstein et al. | 585/751 |
| 5,019,671 A | 5/1991 | Hsu et al. | 585/751 |
| 5,026,951 A | 6/1991 | Schmidt et al. | 585/738 |
| 5,036,035 A | 7/1991 | Baba et al. | 502/221 |
| 5,036,085 A | 7/1991 | Heinemann et al. | 514/361 |
| 5,107,052 A | 4/1992 | McCulloch et al. | 585/738 |
| 5,120,898 A | 6/1992 | Baba et al. | 585/750 |
| 5,146,035 A | 9/1992 | Spehlmann et al. | 585/667 |
| 5,146,037 A | 9/1992 | Zarchy et al. | 585/738 |
| 5,157,199 A | 10/1992 | Soled et al. | 585/750 |
| 5,182,247 A | 1/1993 | Kuhlmann et al. | 502/217 |
| 5,212,136 A | 5/1993 | Angstadt et al. | 502/206 |
| 5,214,017 A | 5/1993 | Angstadt et al. | 502/204 |
| 5,310,868 A | 5/1994 | Angstadt et al. | 585/721 |
| 5,321,197 A | 6/1994 | Angstadt et al. | 585/721 |
| 5,340,465 A | 8/1994 | Gillespie et al. | 208/191 |
| 5,360,534 A | 11/1994 | Rice et al. | 208/139 |
| 5,491,278 A | 2/1996 | Angstadt et al. | 585/731 |
| 5,493,067 A | 2/1996 | Angstadt et al. | 585/731 |
| 5,629,257 A | 5/1997 | Umansky et al. | 502/217 |
| 5,744,684 A | 4/1998 | Zinnen et al. | 585/737 |
| 5,750,459 A | 5/1998 | Marella et al. | 502/304 |
| 5,762,887 A | 6/1998 | Girod et al. | 422/200 |
| 5,762,888 A | 6/1998 | Sechrist | 422/216 |
| 5,768,904 A | 6/1998 | Tagamolila et al. | 62/238.3 |
| 5,780,383 A | 7/1998 | Hollstein et al. | 502/324 |
| 5,786,294 A | 7/1998 | Sachtler et al. | 502/349 |
| 5,802,870 A | 9/1998 | Arnold et al. | 62/480 |
| 5,831,139 A | 11/1998 | Schmidt et al. | 585/315 |
| 5,837,641 A | 11/1998 | Gosling et al. | 502/219 |
| 5,862,060 A | 1/1999 | Murray, Jr. | 364/528.01 |
| 6,180,556 B1 | 1/2001 | Marella et al. | 502/217 |
| 6,184,430 B1 | 2/2001 | Venkatesh et al. | 585/750 |
| 6,214,764 B1 | 4/2001 | Gillespie | 502/230 |
| 6,320,089 B1 | 11/2001 | Gillespie | 585/744 |
| 6,359,179 B1 | 3/2002 | Nemeth et al. | 568/387 |
| 6,448,198 B1 | 9/2002 | Szabo et al. | 502/217 |
| 6,495,733 B1 | 12/2002 | Peratello et al. | 585/743 |
| 6,573,417 B1 | 6/2003 | Rice | 585/738 |
| 6,593,504 B1 | 7/2003 | Bricker et al. | 585/470 |
| 6,706,659 B1 | 3/2004 | Gillespie et al. | 502/217 |
| 2004/0067845 A1 | 4/2004 | Furuta et al. | 502/216 |

OTHER PUBLICATIONS

*Graham v. John Deere Co.*, 383 U.S. 1,148 USPQ 459 (1966).
Ex parte Rubin (POBA 1959) 128 U.S.P.Q. 440.
Cohn v. Comr. Pats. (DCDC 1966) 251 F Supp 378, 148 U.S.P.Q. 486.
In re Boe, 145 U.S.P.Q. 507 (CCPA 1966).
Patent Abstracts of Japan, vol. 011, No. 089 Mar. 19, 1987 & JP 61 242641 A (Res Assoc Util of Light Oil), Oct. 28, 1986 abstract.
Database WPI Section CH, Week 198649 Derwent Publications Ltd., London. GB, AN 1986-323907 XP002222499 & JP 61 242641 A (Keishitsu Ryubun Shinyoto), Oct. 28, 1986 abstract.

* cited by examiner

HIGH-ACTIVITY ISOMERIZATION CATALYST AND PROCESS

CROSS-REFERENCE TO RELATED APPLICATION

This application is a continuation-in-part of our application Ser. No. 10/804,358 filed Mar. 19, 2004, which is a Continuation-In-Part of application Ser. No. 10/717,812, now U.S. Pat. No. 6,881,873 and Ser. No. 10/718,050, now U.S. Pat. No. 6,927,188 both filed Nov. 20, 2003 which applications are a Division and a Continuation, respectively, of application Ser. No. 09/942,237 filed Aug. 29, 2001, now U.S. Pat. No. 6,706,659, the contents of all are hereby incorporated by reference in their entirety.

STATEMENT REGARDING FEDERALLY SPONSORED RESEARCH OR DEVELOPMENT

This work was performed under the support of the U.S. Department of Commerce, National Institute of Standards and Technology, Advanced Technology Program, Cooperative Agreement Number 70NANB9H3035. The United States Government has certain rights in this invention.

FIELD OF THE INVENTION

This invention relates to an improved catalytic composite and process for the conversion of hydrocarbons, and more specifically for the selective upgrading of a paraffinic feedstock by isomerization.

BACKGROUND OF THE INVENTION

The widespread removal of lead antiknock additive from gasoline and the rising fuel-quality demands of high-performance internal-combustion engines have compelled petroleum refiners to install new and modified processes for increased "octane," or knock resistance, in the gasoline pool. Refiners have relied on a variety of options to upgrade the gasoline pool, including higher-severity catalytic reforming, higher FCC (fluid catalytic cracking) gasoline octane, isomerization of light naphtha and the use of oxygenated compounds. Such key options as increased reforming severity and higher FCC gasoline octane result in a higher aromatics content of the gasoline pool at the expense of low-octane heavy paraffins.

Refiners are also faced with supplying reformulated gasoline to meet tightened automotive emission standards. Reformulated gasoline differs from the traditional product in having a lower vapor pressure, lower final boiling point, increased content of oxygenates, and lower content of olefins, benzene and aromatics. Benzene content generally is being restricted to 1% or lower, and is limited to 0.8% in U.S. reformulated gasoline. Gasoline aromatics content is likely to be lowered, particularly as distillation end points (usually characterized as the 90% distillation temperature) are lowered, since the high-boiling portion of the gasoline which thereby would be eliminated usually is an aromatics concentrate. Since aromatics have been the principal source of increased gasoline octanes during the recent lead-reduction program, severe restriction of the benzene/aromatics content and high-boiling portion will present refiners with processing problems. These problems have been addressed through such technology as isomerization of light naphtha to increase its octane number, isomerization of butanes as alkylation feedstock, and generation of additional light olefins as feedstock for alkylation and production of oxygenates using FCC and dehydrogenation. This issue often has been addressed by raising the cut point between light and heavy naphtha, increasing the relative quantity of naphtha to an isomerization unit. The performance of light-naphtha isomerization catalysts thus is increasingly important in refinery economics.

U.S. Pat. No. 2,939,896 B1 teaches isomerization of paraffinic hydrocarbons using a catalyst containing platinum, halogen and a sulfate of aluminum, magnesium and/or zirconium deposited on activated alumina. The patent does not disclose additional metal components of the catalyst, however. U.S. Pat. No. 5,036,035 B1 teaches a catalyst, and its use in isomerization, containing sulfated zirconium oxide or hydroxide and a platinum-group metal. The patent teaches that reduction of the platinum-group metal is not favorable.

U.S. Pat. No. 4,918,041 B1, U.S. Pat. No. 4,956,519 B1 and European Patent Application 0 666 109 A1 disclose a sulfated catalyst, and its use in isomerization, comprising an oxide or hydroxide of Group III or Group IV; oxide or hydroxide of Groups V, VI or VII; and oxide or hydroxide of Group VIII; '109 also discloses a component from a list of Group VIII metals and metal combinations.

U.S. Pat. No. 3,915,845 B1 discloses a catalyst and its use comprising a platinum-group metal, Group IVA metal, halogen and lanthanide in an atomic ratio to platinum-group metal of 0.1 to 1.25. U.S. Pat. No. 5,493,067 B1 teaches that isoparaffins and olefins are alkylated by contact with a solid superacid such as sulfated zirconia optionally containing added metals and containing added heteropolyacids or polyoxoanions.

U.S. Pat. No. 5,310,868 B1 and U.S. Pat. No. 5,214,017 B1 teach catalyst compositions containing sulfated and calcined mixtures of (1) a support containing an oxide or hydroxide of a Group IV-A element, (2) an oxide or hydroxide of a Group VI, VII, or VIII metal, (3) an oxide or hydroxide of a Group I-B, II-B, III-A, III-B, IV-A, V-A metal, and (4) a metal of the lanthanide series.

U.S. Pat. No. 5,212,136 B1 discloses a solid super acid catalyst useful in alkylation processes comprising sulfated and calcined mixtures of a support of an oxide or hydroxide of a Group IV-A element, an oxide or hydroxide of molybdenum, and an oxide or hydroxide of a Group I-B, II-B, III-A, III-B, IV-B, V-A or VI-A metal other than molybdenum or a metal of the lanthanide series.

SUMMARY OF THE INVENTION

A purpose of the present invention is to provide an improved catalyst and process for hydrocarbon conversion reactions. Another purpose of the present invention is to provide improved technology to upgrade naphtha to gasoline. A more specific purpose is to provide an improved catalyst and process for the isomerization of light naphtha to obtain a high-octane gasoline component. This invention is based on the discovery that a catalyst containing ytterbium and platinum components provides superior performance and stability in the isomerization of light naphtha to increase its isoparaffin content.

A broad embodiment of the present invention is directed to a catalyst comprising a sulfated support of an oxide or hydroxide of a Group IVB (IUPAC 4) metal, preferably zirconium oxide or hydroxide, at least a first component which is a lanthanide element or yttrium component, and at least a second component being a platinum-group metal component. The first component preferably consists of a single lanthanide-series element or yttrium and the second component preferably consists of a single platinum-group metal. Preferably, the first component is ytterbium and the second component is platinum. The catalyst optionally contains an inorganic-oxide binder, especially alumina.

An additional embodiment of the invention is a method of preparing the catalyst of the invention by sulfating the Group IVB metal oxide or hydroxide, incorporating a first component, a lanthanide element, yttrium, or any mixture thereof, and the second component, a platinum-group metal, and preferably binding the catalyst with a refractory inorganic oxide.

In another aspect, the invention comprises converting hydrocarbons using the catalyst of the invention. In yet another embodiment, the invention comprises the isomerization of isomerizable hydrocarbons using the catalyst of the invention. The hydrocarbons preferably comprise light naphtha which is isomerized to increase its isoparaffin content and octane number as a gasoline blending stock.

These as well as other embodiments will become apparent from the detailed description of the invention.

Additional objects, embodiments and details of this invention can be obtained from the following detailed description of the invention.

DETAILED DESCRIPTION OF THE INVENTION

The support material of the catalyst of the present invention comprises an oxide or hydroxide of a Group IVB (IUPAC 4) metal, see Cotton and Wilkinson, Advanced Inorganic Chemistry, John Wiley & Sons (Fifth Edition, 1988). Preferably, the metal is selected from zirconium and titanium, with zirconium being especially preferred. The preferred zirconium oxide or hydroxide is converted via calcination to crystalline form. Sulfate is composited on the support material to form, it is believed without so limiting the invention, a mixture of Brönsted and Lewis acid sites. A component of a lanthanide-series element is incorporated into the composite by any suitable means. A platinum-group metal component is added to the catalytic composite by any means known in the art to effect the catalyst of the invention, e.g., by impregnation. Optionally, the catalyst is bound with a refractory inorganic oxide. The support, sulfate, metal components and optional binder may be composited in any order effective to prepare a catalyst useful for the isomerization of hydrocarbons.

Production of the support of the present catalyst may be based on a hydroxide of a Group IVB (IUPAC 4) metal as raw material. For example, suitable zirconium hydroxide is available from MEI of Flemington, N.J. Alternatively, the hydroxide may be prepared by hydrolyzing metal oxy-anion compounds, for example $ZrOCl_2$, $ZrO(NO_3)_2$, $ZrO(OH)NO_3$, $ZrOSO_4$, $TiOCl_2$ and the like. Note that commercial $ZrO(OH)_2$ contains a significant amount of HF, about 1 weight percent. Zirconium alkoxides such as zirconyl acetate and zirconium propoxide may be used as well. The hydrolysis can be effected using a hydrolyzing agent such as ammonium hydroxide, sodium hydroxide, potassium hydroxide, sodium sulfate, $(NH_4)_2HPO_4$ and other such compounds known in the art. The metal oxy-anion component may in turn be prepared from available materials, for example, by treating $ZrOCO_3$ with nitric acid. The hydroxide as purchased or generated by hydrolysis preferably is dried at a temperature of from about 100 to 300° C. to vaporize volatile compounds.

A sulfated support is prepared by treatment with a suitable sulfating agent to form a solid strong acid. Liquid acids whose strength is greater than sulfuric acid have been termed "superacids". A number of liquid superacids are known in the literature including substituted protic acids, e.g., trifluoromethyl substituted $H_2SO_4$, triflic acid and protic acids activated by Lewis acids (HF plus $BF_3$). While determination of the acid strength of liquid superacids is relatively straightforward, the exact acid strength of a solid strong acid is difficult to directly measure with any precision because of the less defined nature of the surface state of solids relative to the fully solvated molecules found in liquids. Accordingly, there is no generally applicable correlation between liquid superacids and solid strong acids such that if a liquid super acid is found to catalyze a reaction, there is no corresponding solid strong acid which one can automatically choose to carry out the same reaction. Therefore, as will be used in this specification, "solid strong acids" are those that have an acid strength greater than sulfonic acid resins such as Amberlyst®-15. Additionally, since there is disagreement in the literature whether some of these solid acids are "superacids" only the term solid strong acid as defined above will be used herein. Another way to define a solid strong acid is a solid comprising of interacting protic and Lewis acid sites. Thus, solid strong acids can be a combination of a Bronsted (protonic) acid and a Lewis acid component. In other cases, the Bronsted and Lewis acid components are not readily identified or present as distinct species, yet they meet the above criteria.

Sulfate ion is incorporated into a catalytic composite, for example, by treatment with sulfuric acid in a concentration usually of about 0.0–10N and preferably from about 0.1–5N. Compounds such as hydrogen sulfide, mercaptans or sulfur dioxide, which are capable of forming sulfate ions upon calcining, may be employed as alternative sources. Preferably, ammonium sulfate is employed to provide sulfate ions and form a solid strong acid catalyst. The sulfur content of the finished catalyst generally is in the range of about 0.5 to 5 mass-%, and preferably is from about 1 to 2.5 mass-%. The sulfated composite is dried, preferably followed by calcination at a temperature of about 500 to 700° C. particularly if the sulfation is to be followed by incorporation of the platinum-group metal.

A first component, comprising one or more of the lanthanide-series elements, yttrium, or mixtures thereof, is another essential component of the present catalyst. Included in the lanthanide series are lanthanum, cerium, praseodymium, neodymium, promethium, samarium, europium, gadolinium, terbium, dysprosium, holmium, erbium, thulium, ytterbium and lutetium. Preferred lanthanide series elements include lutetium, ytterbium, thulium, erbium, holium, terbium, and mixtures thereof. Ytterbium is a most preferred component of the present catalyst, and it is especially preferred that the first component consists essentially of an ytterbium component. The first component may in general be present in the catalytic composite in any catalytically available form such as the elemental metal, a compound such as the oxide, hydroxide, halide, oxyhalide, carbonate or nitrate or in chemical combination with one or more of the other ingredients of the catalyst. The first component is preferably an oxide, an intermetallic with platinum, a sulfate, or in the zirconium lattice. The materials are generally calcined between 600 and 700° C. and thus in the oxide form. Although it is not intended to so restrict the present invention, it is believed that best results are obtained when the first component is present in the composite in a form wherein substantially all of the lanthanide or yttrium component is in an oxidation state above that of the elemental state such as in the form of the oxide, oxyhalide or halide or in a mixture thereof and the subsequently described oxidation and reduction steps that are preferably used in the preparation of the instant catalytic composite are specifically designed to achieve this end. The lanthanide element or yttrium component can be incorporated into the catalyst in any amount which is catalytically effective, suitably from about 0.01 to about 10 mass-% lanthanide or yttrium, or mixtures, in the catalyst on an elemental basis. Best results usually are achieved with about 0.5 to about 5 mass-% lanthanide or yttrium, calculated on an elemental basis. The preferred atomic ratio of lanthanide or yttrium to platinum-group metal for this catalyst is at least about 1:1, preferably about 2:1 or greater, and especially about 5:1 or greater.

The first component is incorporated in the catalytic composite in any suitable manner known to the art, such as by coprecipitation, coextrusion with the porous carrier material, or impregnation of the porous carrier material either before, after, or simultaneously with sulfate though not necessarily with equivalent results. For ease of operation, it is preferred to simultaneously incorporate the lanthanide element or yttrium with the sulfate. It is most preferred to incorporate the platinum-group metal component last. As to the lanthanide series element or yttrium and the platinum-group metal, the order between the two does not have a significant impact.

One method of depositing the first component involves impregnating the support with a solution (preferably aqueous) of a decomposable compound of the lanthanide element or elements or yttrium. By decomposable is meant that upon heating, the lanthanide element or yttrium compound is converted to the lanthanide element or yttrium element or oxide with the release of byproducts. Illustrative of the decomposable compounds of the lanthanide elements are suitable lanthanide complexes or compounds such as, nitrates, halides, sulfates, acetates, organic alkyls, hydroxides, and the like compounds. The first component can be impregnated into the carrier either prior to, simultaneously with, or after the platinum-group metal component, although not necessarily with equivalent results.

A second component, a platinum-group metal, is an essential ingredient of the catalyst. The second component comprises at least one of platinum, palladium, ruthenium, rhodium, iridium, or osmium; platinum is preferred, and it is especially preferred that the platinum-group metal consists essentially of platinum. The platinum-group metal component may exist within the final catalytic composite as a compound such as an oxide, sulfide, halide, oxyhalide, etc., in chemical combination with one or more of the other ingredients of the composite or as the metal. Amounts in the range of from about 0.01 to about 2-wt. % platinum-group metal component, on an elemental basis, are preferred. Best results are obtained when substantially all of the platinum-group metal is present in the elemental state.

The second component, a platinum-group metal component, is deposited on the composite using the same means as for the first component described above. Illustrative of the decomposable compounds of the platinum group metals are chloroplatinic acid, ammonium chloroplatinate, bromoplatinic acid, dinitrodiamino platinum, sodium tetranitroplatinate, rhodium trichloride, hexa-amminerhodium chloride, rhodium carbonylchloride, sodium hexanitrorhodate, chloropalladic acid, palladium chloride, palladium nitrate, diamminepalladium hydroxide, tetraamminepalladium chloride, hexachloroiridate (IV) acid, hexachloroiridate (III) acid, ammonium hexachloroiridate (III), ammonium aquohexachloroiridate (IV), ruthenium tetrachloride, hexachlororuthenate, hexa-ammineruthenium chloride, osmium trichloride and ammonium osmium chloride. The second component, a platinum-group component, is deposited on the support either before, after, or simultaneously with sulfate and/or the first component though not necessarily with equivalent results. It is preferred that the platinum-group component is deposited on the support either after or simultaneously with sulfate and/or the first component.

In addition to the first and second components above, the catalyst may optionally further include a third component of iron, cobalt, nickel, rhenium or mixtures thereof. Iron is preferred, and the iron may be present in amounts ranging from about 0.1 to about 5-wt. % on an elemental basis. The third component, such as iron, may function to lower the amount of the first component, such as ytterbium, needed in the optimal formulation. The third component may be deposited on the composite using the same means as for the first and second components as described above. When the third component is iron, suitable compounds would include iron nitrate, iron halides, iron sulfate and any other soluble iron compound.

The catalytic composite described above can be used as a powder or can be formed into any desired shapes such as pills, cakes, extrudates, powders, granules, spheres, etc., and they may be utilized in any particular size. The composite is formed into the particular shape by means well known in the art. In making the various shapes, it may be desirable to mix the composite with a binder. However, it must be emphasized that the catalyst may be made and successfully used without a binder. The binder, when employed, usually comprises from about 0.1 to 50 mass-%, preferably from about 5 to 20 mass-%, of the finished catalyst. The art teaches that any refractory inorganic oxide binder is suitable. One or more of silica, aluminas, silica-alumina, magnesia, zirconia, and mixtures thereof are suitable binder materials of the present invention. A preferred binder material is alumina, with eta- and/or especially gamma-alumina being favored. Examples of binders which can be used include but are not limited to alumina, silica, silica-alumina, zirconia, and mixtures thereof. Usually the composite and optional binder are mixed along with a peptizing agent such as HCl, $HNO_3$, KOH, etc. to form a homogeneous mixture which is formed into a desired shape by forming means well known in the art. These forming means include extrusion, spray drying, oil dropping, marumarizing, conical screw mixing, etc. Extrusion means include screw extruders and extrusion presses. The forming means will determine how much water, if any, is added to the mixture. Thus, if extrusion is used, then the mixture should be in the form of a dough, whereas if spray drying or oil dropping is used, then enough water needs to be present in order to form a slurry. These particles are calcined at a temperature of about 260° C. to about 650° C. for a period of about 0.5 to about 2 hours.

One embodiment of the catalyst that results in enhanced activity involves having both the lanthanide series component or yttrium component (first component) and the platinum-group metal component (second component) on the binder as well as on the Group IVB (IUPAC 4) sulfated support. For example, in this embodiment, sulfated zirconia and alumina mixed and shaped together may make up the support and the lanthanide series component or yttrium component (first component) as well as the platinum-group metal component (second component) may be present on both the sulfated zirconia and the alumina of the shaped support. Specifically, one catalyst may be sulfated and alumina mixed together and formed into an shaped support with platinum and ytterbium deposited on the mixed shaped support and therefore present on both the sulfated zirconia as well as on the alumina. In this embodiment one process of making the catalyst is as follows.

The sulfated Group IVB (IUPAC 4) support is prepared as discussed above. The sulfated support is mixed with a binder such as those described above. In this embodiment the mixing of the sulfated support and the binder is performed before the addition of the first and second components of the catalytic composite. The mixing may be accomplished by stirring, kneading, mulling, chopping or slurrying. Multiple mixing techniques may be used either sequentially or concurrently. The mixing step is preferably under dry conditions such as close to the incipient wetness of the mixture. A binding agent may be incorporated as well. The mixture is shaped through commonly known forming means as discussed earlier. The shaped support may be calcined at this point of the preparation at temperatures ranging from about 100 to about 900° C. for from about 1 to about 10 hours.

The first and second components may then be added to the shaped and calcined support. As discussed above, the first component may be deposited by impregnating the support with a solution (preferably aqueous) of a decomposable compound of the lanthanide element or elements or yttrium. The second component, a platinum-group metal component, may be deposited on the composite using the same means as for the first component. The first component can be impregnated into the shaped support either prior to, simultaneously with, or after the platinum-group metal component, although not necessarily with equivalent results. If the components are deposited sequentially, the catalytic composite may be dried between impregnation steps. The impregnated shaped support may be calcined at temperatures ranging from about 400 to about 800° C. for form about 0.5 to about 10 hours. The resulting catalyst composite contains the first and second components on both the sulfated Group IVB (IUPAC 4) compound and the binder of the shaped support.

Another process of making the catalyst calls for impregnating the first component into the sulfated Group IVB support before mixing with the binder, shaping and calcining. In this process, the sulfated Group IVB support is prepared as above. The first component is deposited by impregnating the support with a solution (preferably aqueous) of a decomposable compound of the lanthanide element or elements or yttrium. Any suitable impregnation method may be used. The impregnated Group IVB support is then mixed with a binder such as those described earlier. The mixing may be accomplished by any commonly known techniques including those discussed earlier. Multiple mixing techniques may be used in a step-wise manner. The mixing step is preferably under dry conditions such as close to incipient wetness. A binding agent may be incorporated as well. The mixture is shaped through commonly known forming means as discussed earlier. The shaped support may be calcined at temperatures ranging from about 400 to about 900° C. for from about 0.5 to about 10 hours.

After calcination, the second component, a platinum-group metal component, may be deposited on the composite using the same deposition means as for the first component. The impregnated shaped support may be calcined again at temperatures ranging from about 300 to about 650° C. for from about 0.5 to about 10 hours. The resulting catalyst composite contains the platinum-group component on both the sulfated Group IVB (IUPAC 4) compound and the binder of the shaped support while the first component is located primarily on the sulfated Group IVB (IUPAC 4) compound of the support. Due to desorption and re-adsorption that may occur during calcination, a portion of the first component may be located on the binder of the support, but the first component will be primarily located on the sulfated Group IVB (IUPAC 4) compound of the support. It is expected that less than from about 20 to about 30 percent of the first component would be on the binder of the support. One benefit of this embodiment is that a lower overall quantity of the first component is required for the preparation of a suitable catalyst as compared to techniques where the first component is added to the mixture of binder and Group IVB compound. A lower required quantity results in lower raw materials costs, storage costs, and more efficient use of the volume capacity of the equipment used in the preparation.

Alternately, the first component may be deposited on the sulfated support and the binder during or after the mixing step, during or after the forming step and before the first calcination of the shaped support. The platinum-group component is added as above, after the first calcination of the shaped support. The resulting catalytic composite would have the first component and the second component located on both the Group IVB component and on the binder.

The above procedures describe catalyst composites of the present invention formed starting with a sulfated Group IVB component. Therefore, the sulfurous component will be located primarily on the Group IVB component of the support and less so on the binder of the support. With calcination, some of the sulfurous component by means of desorption and re-adsorption may be located on the binder, but it is expected that less than from about 20 to about 30 percent of the sulfurous component would be on the binder. One benefit of the this embodiment is that a lower overall quantity of the sulfurous compound is required for the preparation of a suitable catalyst as compared to techniques such as those described below. A lower required quantity results in lower raw materials costs, storage costs, and more efficient use of the volume capacity of the equipment used in the preparation. Another benefit is the that any undesired interaction between platinum-group metal and the sulfurous compound on the binder is minimized through preferentially locating the sulfurous compound on the Group IVB component and not on the binder. Minimizing such interactions may enhance the activity of the catalytic composite.

However, it is within the scope of the present invention that the sulfurous component may be added at other points of the preparation, although not necessarily with the same results in activity of the resulting catalytic composite. For example the sulfurous component may be added: (1) after the group IVB component and the binder are mixed together; (2) after the group IVB component and the binder are mixed together and shaped; (3) after the group IVB component and the binder are mixed together, shaped and calcined but before the first or second components are deposited; (4) after the group IVB component and the binder are mixed together, shaped, calcined, and simultaneously with the first, second, or both the first and second components.

Yet another embodiment the catalyst of the invention is formed through creating an intimate mixture between a binder impregnated with the first and second components, and the sulfated Group IVB component impregnated with the first and second components. The first and second components are added to the binder and the sulfated Group IVB component as described above in separate processes. A mere mixture of the two catalysts is a physical mixture of from about 20 to about 60 meshed discrete particles as widely practiced by those skillful in the catalyst testing art. The mixture is intimately mixed when both catalyst and binder are meshed and sieved to generate particulates below 100 microns. These fine particulates are thoroughly shaken and mixed then shaped. In the intimate mixture, sulfated zirconia phases and binder phases are in closer contact (tens to a hundred micron range) than in a mere physical mixture (millimeter range) The resulting catalyst contains both the first and second components on Group IVB component and on the binder.

The catalytic composites of the present invention either as synthesized or after calcination can be used as catalysts in hydrocarbon conversion processes. Calcination is required to form zirconium oxide from zirconium hydroxide. Hydrocarbon conversion processes are well known in the art and include cracking, hydrocracking, alkylation of both aromatics and isoparaffins, isomerization, polymerization, reforming, dewaxing, hydrogenation, dehydrogenation, transalkylation, dealkylation, hydration, dehydration, hydrotreating, hydrodenitrogenation, hydrodesulfirization, methanation, ring opening, and syngas shift processes. Specific reaction conditions and the types of feeds, which can be used in these processes, are set forth in U.S. Pat. No. 4,310,440 B1 and U.S. Pat. No. 4,440,871 B1 which are incorporated by reference. A preferred hydrocarbon conversion process is the isomerization of paraffins.

In a paraffin isomerization process, common naphtha feedstocks boiling within the gasoline range contain paraffins, naphthenes, and aromatics, and may comprise small amounts of olefins. Feedstocks which may be utilized include straight-run naphthas, natural gasoline, synthetic naphthas, thermal gasoline, catalytically cracked gasoline, partially reformed naphthas or raffinates from extraction of aromatics. The feedstock essentially is encompassed by the range of a full-range naphtha, or within the boiling point range of 0° to 230° C. Usually the feedstock is light naphtha having an initial boiling point of about 10° to 65° C. and a final boiling point from about 75° to 110° C.; preferably, the final boiling point is less than about 95° C.

The principal components of the preferred feedstock are alkanes and cycloalkanes having from 4 to 7 carbon atoms per molecule ($C_4$ to $C_7$), especially $C_5$ to $C_6$, and smaller amounts of aromatic and olefinic hydrocarbons also may be present. Usually, the concentration of $C_7$ and heavier components is less than about 20 mass-% of the feedstock. Although there are no specific limits to the total content in the feedstock of cyclic hydrocarbons, the feedstock generally contains between about 2 and 40 mass-% of cyclics comprising naphthenes and aromatics. The aromatics contained in the naphtha feedstock, although generally amounting to less than the alkanes and cycloalkanes, may comprise from 2 to 20 mass-% and more usually from 5 to 10 mass-% of the total. Benzene usually comprises the principal aromatics constituent of the preferred feedstock, optionally along with smaller amounts of toluene and higher-boiling aromatics within the boiling ranges described above.

Contacting within the isomerization zones may be effected using the catalyst in a fixed-bed system, a moving-bed system, a fluidized-bed system, or in a batch-type operation. A fixed-bed system is preferred. The reactants may be contacted with the bed of catalyst particles in either upward, downward, or radial-flow fashion. The reactants may be in the liquid phase, a mixed liquid-vapor phase, or a vapor phase when contacted with the catalyst particles, with excellent results being obtained by application of the present invention to a primarily liquid-phase operation. The isomerization zone may be in a single reactor or in two or more separate reactors with suitable means therebetween to ensure that the desired isomerization temperature is maintained at the entrance to each zone. Two or more reactors in sequence are preferred to enable improved isomerization through control of individual reactor temperatures and for partial catalyst replacement without a process shutdown.

Isomerization conditions in the isomerization zone include reactor temperatures usually ranging from about 40° to 250° C. Lower reaction temperatures are generally preferred in order to favor equilibrium mixtures having the highest concentration of high-octane highly branched isoalkanes and to minimize cracking of the feed to lighter hydrocarbons. Temperatures in the range of about 100° to about 200° C. are preferred in the process of the present invention. Reactor operating pressures generally range from about 100 kPa to 10 MPa absolute, preferably between about 0.3 and 4 MPa. Liquid hourly space velocities range from about 0.2 to about 25 $hr^{-1}$, with a range of about 0.5 to 15 $hr^{-1}$ being preferred.

Hydrogen is admixed with or remains with the paraffinic feedstock to the isomerization zone to provide a mole ratio of hydrogen to hydrocarbon feed of from about 0.01 to 20, preferably from about 0.05 to 5. The hydrogen may be supplied totally from outside the process or supplemented by hydrogen recycled to the feed after separation from the reactor effluent. Light hydrocarbons and small amounts of inerts such as nitrogen and argon may be present in the hydrogen. Water should be removed from hydrogen supplied from outside the process, preferably by an adsorption system as is known in the art. In a preferred embodiment, the hydrogen to hydrocarbon mol ratio in the reactor effluent is equal to or less than 0.05, generally obviating the need to recycle hydrogen from the reactor effluent to the feed.

Upon contact with the catalyst, at least a portion of the paraffinic feedstock is converted to desired, higher octane, isoparaffin products. The catalyst of the present invention provides the advantages of high activity and improved stability. When the first component is selected to be ytterbium, the catalyst of the present invention has the additional advantage of increased ring opening activity.

The isomerization zone generally also contains a separation section, optimally comprising one or more fractional distillation columns having associated appurtenances and separating lighter components from an isoparaffin-rich product. Optionally, a fractionator may separate an isoparaffin concentrate from a cyclics concentrate with the latter being recycled to a ring-cleavage zone.

Preferably part or all of the isoparaffin-rich product and/or the isoparaffin concentrate are blended into finished gasoline along with other gasoline components from refinery processing including, but not limited to, one or more of butanes, butenes, pentanes, naphtha, catalytic reformate, isomerate, alkylate, polymer, aromatic extract, heavy aromatics, gasoline from catalytic cracking, hydrocracking, thermal cracking, thermal reforming, steam pyrolysis and coking, oxygenates such as methanol, ethanol, propanol, isopropanol, tert-butyl alcohol, sec-butyl alcohol, methyl tertiary butyl ether, ethyl tertiary butyl ether, methyl tertiary amyl ether and higher alcohols and ethers, and small amounts of additives to promote gasoline stability and uniformity, avoid corrosion and weather problems, maintain a clean engine and improve driveability.

The following examples serve to illustrate certain specific embodiments of the present invention. These examples should not, however, be construed as limiting the scope of the invention as set forth in the claims. There are many possible other variations, as those of ordinary skill in the art will recognize, which are within the scope of the invention.

EXAMPLE 1

Catalyst samples of Table 1 were prepared starting with zirconium hydroxide that had been prepared by precipitating zirconyl nitrate with ammonium hydroxide at 65° C. The zirconium hydroxide was dried at 120° C., ground to 40–60 mesh. Multiple discrete portions of the zirconium hydroxide were prepared. Solutions of either ammonium sulfate or a metal salt (component 1) were prepared and added to the portions of zirconium hydroxide. The materials were agitated briefly and then dried with 80–100° C. air while rotating. The impregnated samples were then dried in a muffle oven at 150° C. for two hours under air. Solutions of either ammonium sulfate or a metal salt (component 2, where component 2 is not the same as component 1) were prepared and added to the dried materials. The samples were briefly agitated and dried while rotating. The samples were then calcined at 600–700° C. for 5 hours. The final impregnation solutions of chloroplatinic acid were prepared and added to the solids. The samples were agitated and dried while rotating as before. The samples were finally calcined at 525° C. in air for 2 hours. In Table 1 below, "A" indicates that catalysts were made at modifier levels of 1 wt. %, 2 wt. %, 3 wt. % and 4 wt. %; "B" indicates that catalysts were made at sulfate levels of 6 wt. %, 7 wt. %, and 8 wt. %; and "C" indicates that catalysts were made at platinum levels of 0.25 wt. %, 0.5 wt. %, 0.75 wt. %, and 1 wt. %.

TABLE 1

| Modifier | Modifier Level | Fe | Pt | SO$_4$ |
|---|---|---|---|---|
| Ce | A | 0 | 0.4 | 7 |
| Dy | A | 0 | 0.4 | 7 |
| Er | A | 0 | 0.4 | 7 |
| Eu | A | 0 | 0.4 | 7 |
| Gd | A | 0 | 0.4 | 7 |
| Ho | A | 0 | 0.4 | 7 |
| La | A | 0 | 0.4 | 7 |
| Lu | A | 0 | 0.4 | 7 |
| Nd | A | 0 | 0.4 | 7 |
| Pr | A | 0 | 0.4 | 7 |
| Sm | A | 0 | 0.4 | 7 |
| Tb | A | 0 | 0.4 | 7 |
| Tm | A | 0 | 0.4 | 7 |
| Y | A | 0 | 0.4 | 7 |
| Yb | 0.3 | 0 | 0.3 | 7 |
| Yb | 0.4 | 0 | 0.4 | 7 |
| Yb | 0.5 | 0 | 0.5 | 7 |
| Yb | 1 | 0 | 0.4 | 7 |
| Yb | 1 | 0 | C | B |
| Yb | 1.8 | 0 | C | B |
| Yb | 2 | 0 | 0.4 | 7 |
| Yb | 2.7 | 0 | C | B |
| Yb | 3 | 0 | 0.375 | 7 |
| Yb | 3 | 0 | 0.4 | 7 |
| Yb | 3.5 | 0 | C | B |
| Yb | 4 | 0 | 0.4 | 7 |
| Ce | 1 | 1 | 0.4 | 7 |
| Ce | 1 | 1.5 | 0.4 | 7 |
| Yb | 1 | 1.5 | 0.4 | 7 |
| Yb | 1 | 2 | 0.4 | 7 |

EXAMPLE 2

Figure 1:
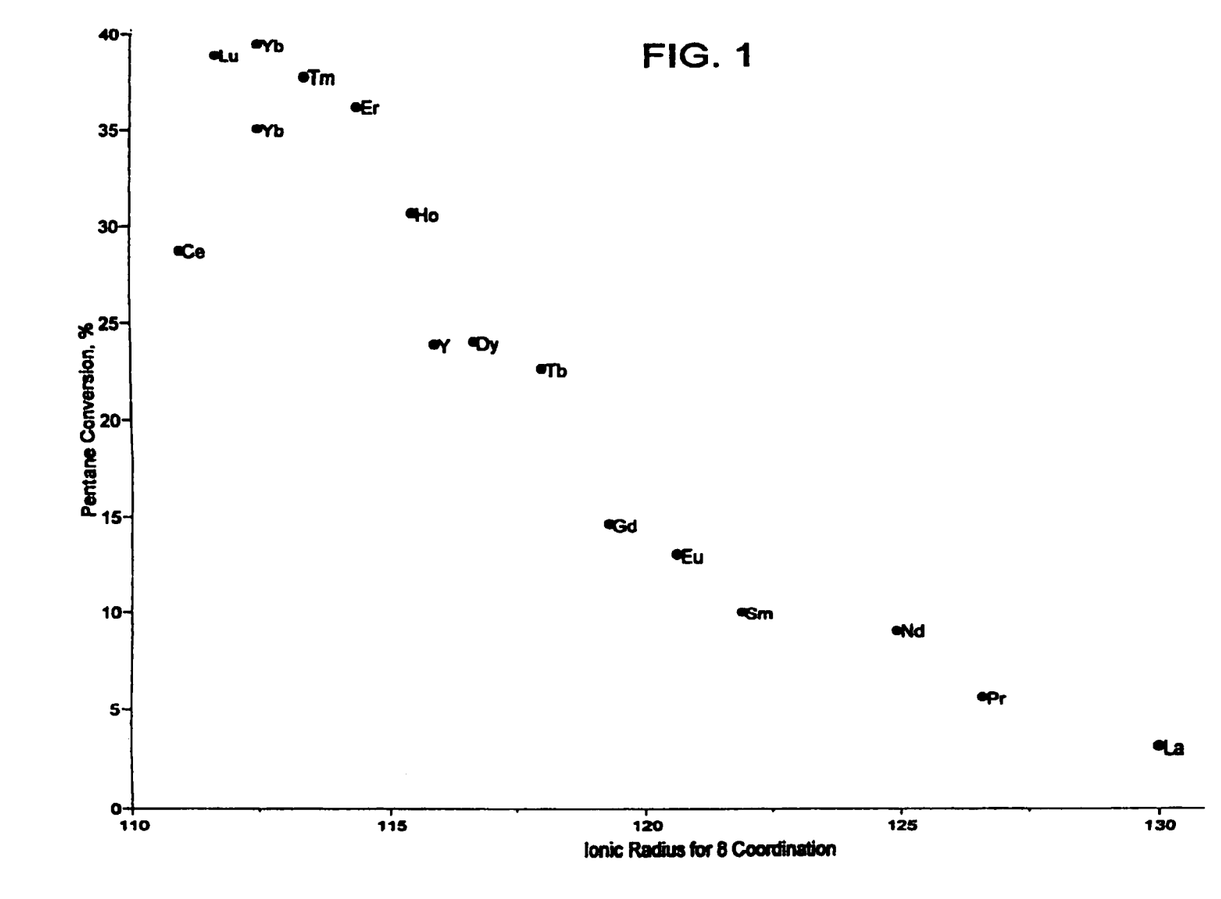
FIG. 1 shows a plot of the percent conversion of pentane versus the ionic radius for 8 coordination of a series of catalysts where the first component of the catalysts was varied.

Catalysts were prepared as described in Example 1 containing 2 wt. % modifier, 0.4-wt. % platinum, and 7-wt. % sulfate. Approximately 95 mg of each sample was loaded into a multi-unit reactor assay. The catalysts were pretreated in air at 450° C. for 2–6 hours and reduced at 200° C. in H$_2$ for 0.5–2 hours. 8 wt. % pentane in hydrogen was then passed over the samples at 150° C., approximately 1 atm, and 2.5 hr$^{-1}$ WHSV (based on pentane only). The products were analyzed using online gas chromatographs and the results are shown in FIG. 1, note that a replicate of the ytterbium-containing catalyst was tested. FIG. 1 is a plot of percent pentane conversion vs. the ionic radii for 8 coordination of the lanthanide series or yttrium materials used to modify a platinum sulfated zirconia catalyst. The ionic radii were determined by reference to Huheey, J. E. Inorganic Chemistry—Principles of Structure and Reactivity, 2nd Ed.; Harper & Row: New York, 1978. The plot shows a maximum conversion around 112 picometers (ytterbium). The activity drops off rapidly as the ionic radius increases above approximately 115 picometers.

EXAMPLE 3

Figure 2:
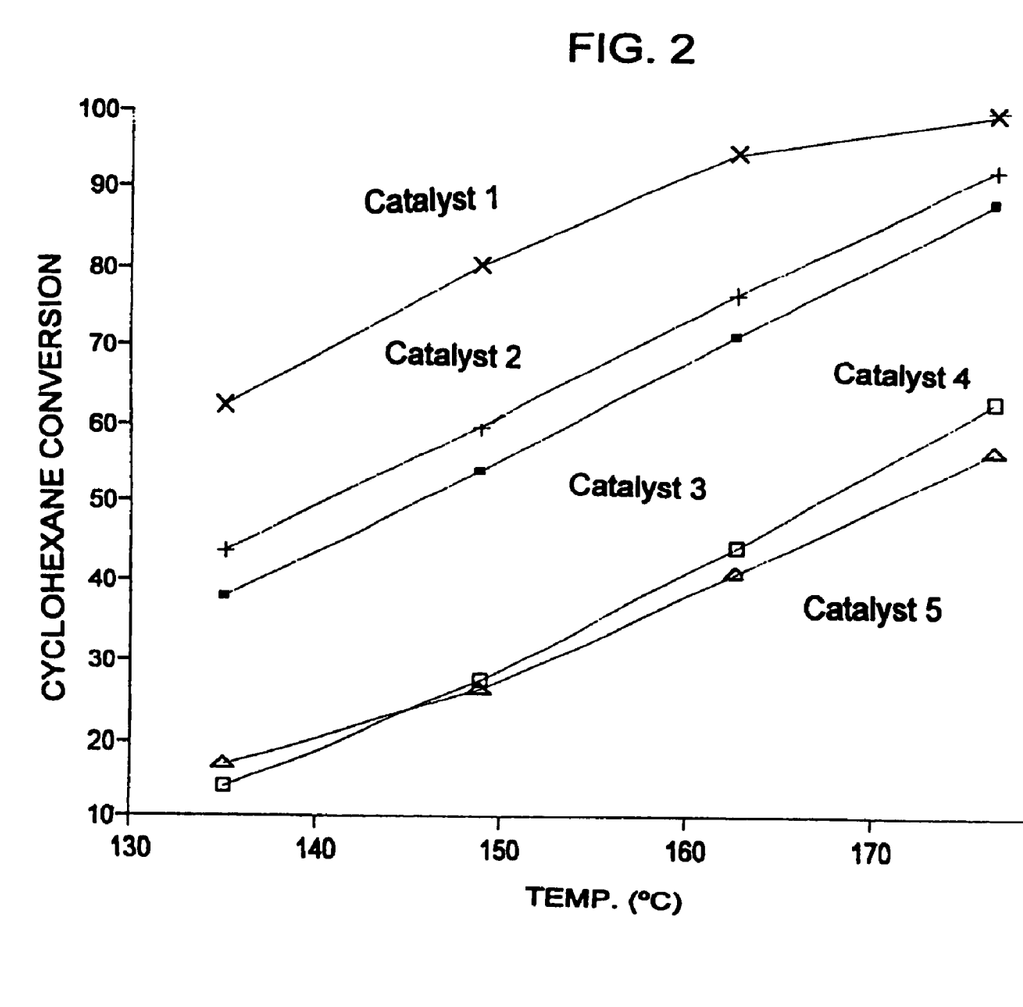
FIG. 2 shows a plot of the cyclohexane conversation versus temperature of a series of catalysts. Catalysts of the present invention are compared to reference catalysts.

Catalysts were prepared as described in Example 1, with the first catalyst (Catalyst 1 in FIG. 2) containing 3 wt. % ytterbium, about 0.375 to about 0.4 wt. % platinum, and 7 wt. % sulfate; the second catalyst (Catalyst 2 in FIG. 2) containing 1 wt. % ytterbium, about 0.375 to about 0.4 wt % platinum, 1 wt. % iron, and 6 wt. % sulfate, and the third catalyst (Catalyst 3 in FIG. 2) containing 0.5 wt. % manganese, 1 wt. % iron, about 0.375 to about 0.4 wt % platinum and 7 wt. % sulfate. Additionally, two reference catalysts were obtained, the first reference catalyst containing platinum on sulfated zirconia (Catalyst 4 in FIG. 2), and the second reference catalyst containing platinum, iron, and manganese on sulfated zirconia (Catalyst 5 in FIG. 2). Approximately 10.5 g of each sample was loaded into a multi-unit reactor assay. The catalysts were pretreated in air at 450° C. for 2–6 hours and reduced at 200° C. in H2 for 0.5–2 hours. Hydrogen and a feed stream containing 36 wt. % n-pentane, 52 wt. % n-hexane, 10 wt. % cyclohexane and 2 wt. % n-heptane was passed over the catalysts at 135° C., 150° C., 163° C., and 176° C., at approximately 450 psig, and 2 $^{-1}$ WHSV. The hydrogen to hydrocarbon molar ratio was 1.3. The products were analyzed using online gas chromatographs and the percent conversion of cyclohexane was determined at the different temperatures. The results are shown in FIG. 2 which shows that significant ring opening capability was demonstrated by the platinum and ytterbium on sulfated zirconia catalyst.

EXAMPLE 4

A sulfated zirconium hydroxide powder purchased from MEI Corp. was co-mulled with pseudo-Boehmite powder. A solution of ytterbium nitrate solution was spray impregnated on the mixture while maintaining the water content to be below the incipient wetness point of the mixture. The impregnated and formed materials were then dried in air and calcined in air at 650° C. Platinum was loaded on the material via wet impregnation, followed by calcination at 500° C. The preparation was repeated at different levels of platinum and ytterbium as sown in Table 2. An analysis of a resulting catalyst demonstrated the 40% of the platinum, 10% of the sulfate, and 10% of the ytterbium were located on the alumina binder and 60% of the platinum, 90% of the sulfate, and 90% of the ytterbium were located on the sulfated zirconia.

EXAMPLE 5

A binderless catalyst according to this invention was made in a process similar to Example 4. A MEI sulfated zirconium hydroxide powder was mulled while a solution of ytterbium nitrate solution was sprayed impregnated. The water content was maintained to be below the incipient wetness point of the mixture. The impregnated materials were then dried at 100° C. overnight in air, followed by calcination in air at 650° C. Platinum was loaded on the material via impregnation, followed by calcination at 500° C. Key composition data are listed in Table 2. This catalyst has all of the sulfate, platinum and ytterbium on the zirconia phase.

EXAMPLE 6

Catalysts prepared in Examples 4 and 5 were tested at the same conditions as described in Example 3. The mole ratio of 2,2-dimethylbutane (2,2DMB) to total hexane isomers is defined as, $$2,2DMB/C6s = \frac{2,2DMB \text{ mole \% in product}}{\text{Sum of } C6 \text{ isomers mole \% in product}} \times 100\%$$

was used as an indicator of catalysts activity and product quality. The resulting test data are summarized in Table 2. The results show neither binderless ytterbium-modified catalyst nor a simple mixture of sulfated zirconia and binder catalysts at tens of micron levels yield the high performance of invented catalysts. Invented catalyst possesses unique synergistic effect of binder and sulfated zirconia phases.

TABLE 2

| Example | % Pt | % Yb | % S | % Binder | % 2,2DMB/C6s @ 162° C. |
|---|---|---|---|---|---|
| 4-A | 0.35 | 4.8 | 1.7 | 20 | 24.7 |
| 4-B | 0.35 | 1.0 | 1.7 | 20 | 21.1 |
| 5 | 0.43 | 3.0 | 1.8 | 0 | 21.6 |

EXAMPLE 7

Mixed particles of sulfated zirconia and alumina binder catalysts were prepared as described below.

Model binder catalyst was prepared as follows. Pseudoboehmite powder was mulled and impregnated with ytterbium nitrate and ammonium sulfate solution. The resulting mixture is calcined at 650° C. for 4 hours. Platinum was loaded on the material via impregnating chloroplatinic acid solution, followed by calcination at 500° C. to yield binder catalyst.

Binder catalyst as described in above was ground in a ceramic mortal with a ceramic pestle. The fines were sieved to yield powder sized to below 150 mesh (<100 micron). The powder was intimately mixed with sulfated zirconia catalyst powder generated according to Example 5 in selected ratios to yield certain alumina, ytterbium, or platinum concentrations. The powder mixture was pressed at 5000–7500 psig and sized to yield 20–60 mesh particles suitable for paraffin isomerization pilot plant tests.

What is claimed is:

1. A catalyst comprising a support comprising a sulfated oxide or hydroxide of at least one of the elements of Group IVB (IUPAC 4) of the Periodic Table, having deposited thereon; a first component selected from the group consisting of a lanthanide element, mixtures thereof, and yttrium; and a second component comprising at least one platinum-group metal component, said catalyst further comprising from about 2 to about 50 mass-% of a refractory inorganic-oxide binder having deposited thereon at least one platinum-group metal component.

2. The catalyst of claim 1 wherein the first component comprises from about 0.01 to 10 mass-%, on an elemental basis, of the catalyst.

3. The catalyst of claim 1 wherein the second component comprises from about 0.01 to 2 mass-%, on an elemental basis, of the catalyst.

4. The catalyst of claim 1 wherein the element of Group IVB (IUPAC 4) comprises zirconium and the refractory inorganic-oxide binder comprises alumina.

5. The catalyst of claim 1 wherein the catalyst comprises from about 0.5 to 5 mass-% sulfur on an elemental basis.

6. The catalyst of claim 1 wherein the atomic ratio of the first component to the second component is at least about 2.

7. The catalyst of claim 1 wherein the first component is selected from the group consisting of lutetium, ytterbium, thulium, erbium, holium, yttrium, terbium, and combinations thereof.

8. The catalyst of claim 7 wherein the first component is ytterbium.

9. The catalyst of claim 1 further comprising a third component selected from the group consisting of iron, cobalt, nickel, rhenium, and mixtures thereof.

10. The catalyst of claim 9 wherein the third component is iron in an amount from about 0.1 to about 5 wt. %.

11. The catalyst of claim 1 wherein the second component is platinum.

12. A hydrocarbon conversion catalyst comprising a support comprising a sulfated oxide or hydroxide of zirconium having deposited thereon; from about 0.01 to 10 mass-%, on an elemental basis, of a lanthanide component selected from the group consisting of ytterbium, lutetium, thulium, and mixtures thereof; and from about 0.01 to 2 mass-%, on an elemental basis, of a platinum component, said catalyst further comprising from about 2 to about 50 mass-% of a refractory inorganic-oxide binder having deposited thereon from about 0.01 to about 2 mass-%, on an elemental basis, of a platinum component.

13. A process for the preparation of a catalyst suitable for hydrocarbon conversion comprising a sulfated support comprising at least one of the oxides and hydroxides of the elements of Group IVB (IUPAC 4) of the Periodic Table, a first component selected from the group consisting of a lanthanide-series element, mixtures thereof, and yttrium, and a second component selected from the group of platinum-group metals and mixtures thereof said catalyst further comprising from about 2 to about 50 mass-% of a refractory inorganic-oxide binder having deposited thereon at least one platinum-group metal component, the process comprising sulfating an oxide or hydroxide of at least one element of Group IVB (IUPAC 4) of the Periodic Table to form a sulfated support; depositing on the sulfated support, the first component; mixing with a refractory inorganic-oxide binder to form a mixture and calcining at a first temperature, and then depositing the second component and calcining at a second temperature to form said catalyst.

14. The process of claim 13 further comprising shaping the mixture prior to calcining at the first temperature.

15. A process for the preparation of a catalyst suitable for hydrocarbon conversion comprising a sulfated support comprising at least one of the oxides and hydroxides of the elements of Group IVB (IUPAC 4) of the Periodic Table, a first component selected from the group consisting of a lanthanide-series element, mixtures thereof, and yttrium, and a second component selected from the group of platinum-group metals and mixtures thereof said catalyst further comprising from about 2 to about 50 mass-% of a refractory inorganic-oxide binder having deposited thereon at least one platinum-group metal component, the process comprising sulfating an oxide or hydroxide of at least one element of Group IVB (IUPAC 4) of the Periodic Table to form a sulfated support; mixing with a refractory-inorganic oxide binder to form a mixture; depositing on the mixture, the first component; calcining at a first temperature, and then depositing the second component and calcining at a second temperature to form said catalyst.

16. The process of claim 15 further comprising shaping the mixture having the first component deposited thereon prior to calcining at the first temperature.

17. A process for the preparation of a catalyst suitable for hydrocarbon conversion comprising a sulfated support comprising at least one of the oxides and hydroxides of the elements of Group IVB (IUPAC 4) of the Periodic Table mixed with a refractory-oxide binder, a first component selected from the group consisting of a lanthanide-series element, mixtures thereof, and yttrium, and a second component selected from the group of platinum-group metals and mixtures thereof, the process comprising sulfating an oxide or hydroxide of at least one element of Group IVB (IUPAC 4) of the Periodic Table to form a sulfated support; mixing with a refractory-inorganic oxide binder to form a mixture; calcining at a first temperature, and then depositing the first and second components and calcining at a second temperature to form said catalyst.

18. The process of claim 17 further comprising shaping the mixture prior to calcining at the first temperature.

19. A process for converting hydrocarbons by contacting a feed with a solid acid catalyst, comprising a support comprising a sulfated oxide or hydroxide of at least an element of Group IVB (IUPAC 4) of the Periodic Table, a first component selected from the group consisting of a lanthanide-series element, mixtures thereof, and ytterbium, and a second component selected from the group of platinum-group metals and mixtures thereof, said catalyst further comprising from about 2 to about 50 mass-% of a refractory inorganic-oxide binder having deposited thereon at least one platinum-group metal component, to give a converted product.

20. The process of claim 19 wherein the hydrocarbon conversion process is selected from the group consisting of cracking, hydrocracking, aromatic alkylation, isoparaffin alkylation, isomerization, polymerization, reforming, dewaxing, hydrogenation, dehydrogenation, transalkylation, dealkylation, hydration, dehydration, hydrotreating, hydrodenitrogenation, hydrodesulfurization, methanation, ring opening, and syngas shift.

21. The process of claim 19 wherein the atomic ratio of the first component to the second component is at least about 2.

22. The process of claim 19 wherein the first component is selected from the group consisting of ytterbium, lutetium, thulium, or mixtures thereof and the second component is platinum.

23. The process of claim 19 wherein the catalyst further comprises a third component selected from the group consisting of iron, cobalt, nickel, rhenium, and mixtures thereof.

24. A process for the isomerization of a paraffinic feedstock to obtain a product having an increased isoparaffin content comprising contacting the paraffinic feedstock in an isomerization zone maintained at isomerization conditions comprising a temperature of from 40 to 250° C., pressure of from 100 kPa to 10 MPa and liquid hourly space velocity of from 0.2 to 25 hr$^{-1}$ with a solid acid isomerization catalyst, comprising a sulfated support comprising an oxide or hydroxide of elements of Group IVB (IUPAC 4) of the Periodic Table, a first component selected from the group consisting of a lanthanide-series element mixtures thereof, and ytterbium, and a second component selected from the group of platinum-group metals and mixtures thereof, said catalyst further comprising from about 2 to about 50 mass-% of a refractory inorganic-oxide binder having deposited thereon at least one platinum-group metal component, and recovering an isoparaffin-rich product.

25. The process of claim 24 wherein the isomerization conditions comprise a temperature from about 100 to about 200° C., a pressure from about 300 kPa to about 4 MPa, and a liquid hourly space velocity of from 0.5 to 15 hr$^{-1}$, and wherein free hydrogen is present in the isomerization zone in an amount from about 0.05 to 5 moles per mole of $C_5$+ hydrocarbons present in the zone.

26. The process of claim 25 wherein the refractory inorganic-oxide binder comprises alumina.

27. The process of claim 24 further comprising blending at least a portion of the isoparaffin-rich product with another gasoline component to form a blended gasoline product.

* * * * *